United States Patent [19]

Pearce et al.

[11] Patent Number: 5,775,026
[45] Date of Patent: Jul. 7, 1998

[54] INSECT BAIT AND CONTROL STATION

[75] Inventors: Robert C. Pearce, Arlington; Robby C. Murdock, Flower Mound; Amy E. Thompson, Arlington; Scott M. Reed, Flower Mound; Don E. Wallace, Rockwall, all of Tex.

[73] Assignee: Novartis AG, Basel, Switzerland

[21] Appl. No.: 624,297

[22] Filed: Mar. 29, 1996

[51] Int. Cl.⁶ .................................................. A01M 25/00
[52] U.S. Cl. ............................................. 43/132.1; 43/124
[58] Field of Search ........................... 43/124, 131, 132.1

[56] References Cited

U.S. PATENT DOCUMENTS

| | | |
|---|---|---|
| 3,993,648 | 11/1976 | Powell . |
| 4,065,560 | 12/1977 | Powell . |
| 4,310,985 | 1/1982 | Foster et al. . |
| 4,804,142 | 2/1989 | Riley ........................... 43/131 |
| 4,879,837 | 11/1989 | Capizzi et al. ............... 43/124 |
| 4,908,977 | 3/1990 | Foster . |
| 4,947,578 | 8/1990 | Anderson ..................... 43/131 |
| 5,046,280 | 9/1991 | Foster et al. . |
| 5,150,541 | 9/1992 | Foster et al. . |
| 5,379,545 | 1/1995 | Gall .............................. 43/131 |
| 5,396,730 | 3/1995 | Van Gundy et al. ......... 43/131 |
| 5,399,344 | 3/1995 | Yang et al. . |

*Primary Examiner*—Kurt Rowan
*Attorney, Agent, or Firm*—Michael P. Morris; M. Henry Heines

[57] ABSTRACT

A bait station for attracting and killing insects with a nithiazine-type insecticide is constructed in a substantially flat configuration, with the insecticide formulated as a solid coating on the surface of a solid sheet of moisture-free nonabsorptive material, the station further containing one or more ampoules of an attractant composition. The coated sheet and ampoules are held in a housing, with the ampoules in a compressible portion of the housing permitting them to be manually broken to discharge their contents on command, the housing containing appropriately positioned openings to both expose the insecticide surface and to permit release of the attractant vapors.

12 Claims, 3 Drawing Sheets

INSECT BAIT AND CONTROL STATION

This invention resides in the field of insect control devices, particularly those used for luring and killing flies.

BACKGROUND OF THE INVENTION

Tetrahydro-2-(nitromethylene)-2H-1,3-thiazines are a class of compounds known to be useful for the control of insect larvae of the genus Heliothis, such as the corn earworm, the cotton bollworm, the tomato fruitworm, and the tobacco budworm; the genus Agrotis, such as the black cutworm; the genus Trichoplusia, such as the cabbage looper; and the genus Spodoptera, such as the Egyptian cotton leafworm; as well as various types of flies such as the whitefly (Aleyrodidae spp.), the house fly (*Musca domestica*), the little house fly (Fannia spp.), the bush fly (*Musca vertustissima*), the blow fly (*Calliphora vomitoria*), the fruit fly (*Drosophila melanogaster*), and the stable fly (*Stromoxys calcitrans*). Disclosures of tetrahydro-2-(nitromethylene)-2H-1,3-thiazines appear in U.S. Pat. Nos. 3,993,648 to Powell, J. E. (Shell Oil Company, Nov. 23, 1976), and 4,065,560 to Powell, J. E. (Shell Oil Company, Dec. 27, 1977), the disclosures of both of which are incorporated herein by reference. These patents define this class of compounds as resonance hybrids of the following two forms:

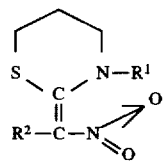
(A)

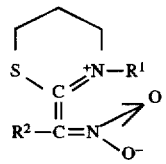
(B)

in which:

R$^1$ is either hydrogen or a one- to eight-carbon atom containing group that is one of the following: alkyl, alkenyl, alkoxyalkyl, cycloalkyl, cyanoalkyl, haloalkenyl, phenylalkyl, or alkoxycarbonylvinyl; and R$^2$ is either hydrogen or:
  a one- to eight-carbon atom containing group that is one of the following:
    alkyl, alkenyl, alkynyl, haloalkyl, haloalkenyl, halo(hydroxy)alkyl, alkoxyalkyl, cycloalkyl, cyanoalkyl, hydroxyalkyl, alkoxycarbonylalkyl, alkylthioalkyl, alkylsulfinylalkyl, phenylalkyl, phenylthio optionally substituted on the ring by one or more of halogen, nitro, cyano, alkyl, phenyl, alkoxy or phenoxy,
  halogen,
  aminomethyl, where the amino group is optionally substituted with alkyl, hydroxyalkyl, alkoxyalkyl, cycloalkyl, alkenyl, phenyl, or phenylalkyl, and various heterocyclic moieties where the hetero atoms are oxygen, sulfur or nitrogen.

The most prominent compound of this class is tetrahydro-2-(nitromethylene)-2H-1,3-thiazine itself, in which both R$^1$ and R$^2$ are H. This compound is commonly known as nithiazine and has the formula

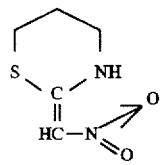

Fly traps incorporating insecticides of this and other classes have been designed in elaborate ways to attract the flies and retain them long enough to kill them, then to remove them to maintain continuous access to the active ingredient as further flies approach the trap. Cavities, reservoirs, sloping surfaces, and strategically placed passages have been used to achieve these results. Aside from the cost of manufacturing traps of this type and the storage space consumed by them until their use is desired, these traps have the added disadvantage of a limited shelf life. Tetrahydro-2-(nitromethylene)-2H-1,3-thiazine insecticides are unstable in the presence of moisture. Their effect diminishes rapidly even in storage, since the fly trap construction often involves the use of porous materials which adsorb and retain moisture. Insect lures have been incorporated into the fly trap construction to enhance their effectiveness, but these lures are volatile and offer a diminishing effect themselves.

SUMMARY OF THE INVENTION

The present invention provides a device for attracting and killing insects, notably flies of the various types listed above, with tetrahydro-2-(nitromethylene)-2H-1,3-thiazine insecticides, such device overcoming many of the disadvantages of the devices of the prior art. Included among the characteristic features of this device are the insecticide formulated as a solid coating on the surface of a solid sheet of moisture-free nonabsorptive material, an attractant composition encapsulated in one or more breakable shells, and a housing which retains both the sheet and the shells containing the attractant composition, with openings arranged to serve both as access to the sheet and as ports for the discharge of vaporized attractant to the atmosphere adjacent to the sheet. The breakable shells are retained in one or more cavities in the housing whose walls are compressible to permit breakage of the shells by manual pressure on the housing walls without manual contact with the shells or the attractant.

The housing itself is flat and substantially planar, at least the portions that do not house the breakable shells of attractant. This permits space-efficient storage and packaging. The attractant shells remain unbroken until the device is placed in use, at which time the attractant is released by manually breaking one of the shells. When two or more attractant shells are included, prolongation of their effectiveness is achieved by breaking them individually at intervals related to their decline in effectiveness as their contents volatilize and escape.

Details of these and other features and advantages of the invention will become apparent from the description that follows.

DETAILED DESCRIPTION OF THE INVENTION AND PREFERRED EMBODIMENTS

Figure 1:
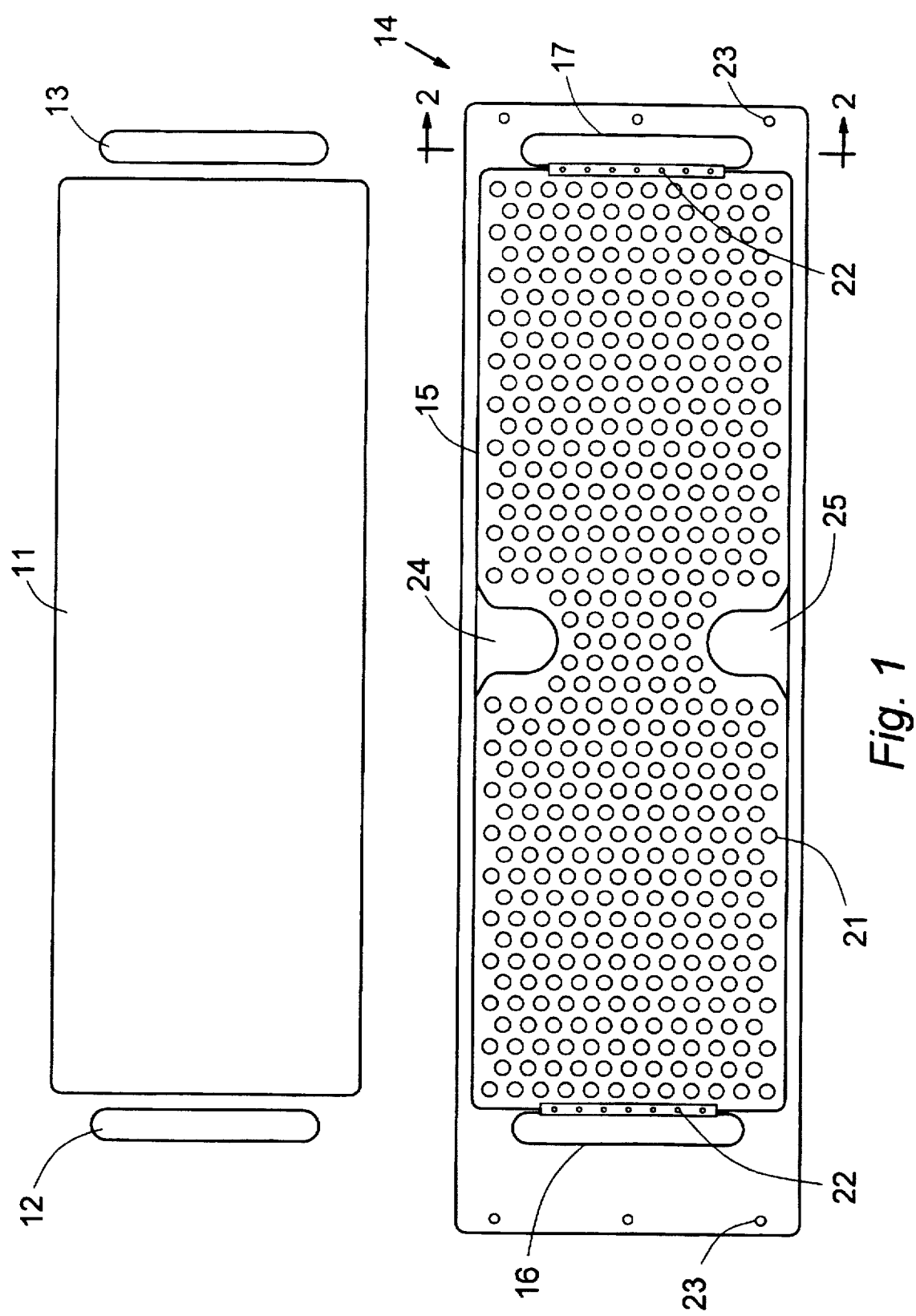
FIG. 1 is a plan view of one example of a device for attracting and killing insects in accordance with this invention, separated into its component parts.

While the insecticides that are useful in the practice of this invention include tetrahydro-2-(nitromethylene)-2H-1,3-thiazines in general as defined by Formulas A and B above, certain subclasses of these formulas are preferred. In particular, $R^1$ is preferably a hydrogen atom, an alkyl group (preferred alkyls are $C_1$–$C_3$ alkyl), or an alkenyl group (preferred alkenyls are vinyl and allyl). Likewise, $R^2$ is preferably a hydrogen atom, an alkyl group (again, preferred alkyls are $C_1$–$C_3$ alkyl), an alkenyl group (again, preferred alkenyls are vinyl and allyl), or a halogen atom. Nithiazine, in which $R^1$ and $R^2$ are both hydrogen atoms, is the most preferred. Nithiazine itself is a pale yellow crystalline solid.

In addition to nithiazine or one of its analogs, the insecticide formulation as prepared for application to the solid sheet substrate preferably contains one or more additional components serving as diluents or carriers, stabilizers, preservatives, viscosity modifiers, plasticizers, binders, dyes to impart a color to the coating, preferably a lighter color than the housing or solvents to facilitate application to the substrate. Preferred formulations contain a combination of these types of additives. All such additives can be selected from materials well known for these purposes and readily available from chemical suppliers, and the choice of specific materials, of the combinations of types of materials, and of the proportions of each will be well within the routine expertise of those skilled in pesticide formulations.

One presently preferred example of a nithiazine formulation for application to a solid sheet substrate is as follows:

| Ingredient | Parts by Weight | Function |
| --- | --- | --- |
| Nithiazine technical (97%) | 1.03 | Active ingredient |
| Powdered sucrose | 17.13 | Diluent/carrier |
| Ca(OH)$_2$ | 0.30 | Stabilizer |
| Carrageenan | 0.40 | Thickener |
| Sodium propionate | 0.10 | Preservative |
| Pigment Yellow 1 Toner | 0.04 | Colorant |
| Denatured ethyl alcohol | 28.00 | Solvent |
| Polyvinylpyrrolidone K-120 | 0.80 | Binder |
| Polyethylene glycol #400 | 0.20 | Plasticizer |

Preparation of the formulation in liquid form for application to the substrate is readily achieved by methods commonly used among formulations chemists. One example of such a method, using the ingredients listed above, begins with the comminution of the nithiazine and Ca(OH)$_2$ together to a fine particle size in a roller mill or other suitable fine grinding mill. The resulting powder is then mixed with the sugar, the carrageenan, the sodium propionate, and the yellow toner in an appropriate blender such as a planetary blender, a ribbon blender, or a twin-shell blender, until the mixture is uniform in color. The mixture is then milled and passed through a 100-mesh sieve. In a separate vessel, the polyethylene glycol and the polyvinylpyrrolidone are dissolved in the alcohol. The dry blended solids are added to the resulting liquid solution and mixed to form a uniform slurry that can be applied directly to the substrate.

Materials suitable for the substrate include any solid material that is inert with respect to the active ingredient and with respect to any of the additives present in the formulation of the active ingredient, and that is either nonporous and hence non-retentive of atmospheric moisture, or coated with a non-porous coating underlying the coating layer of active ingredient and sealing off any pores in the core material. While coated papers can be used, the preferred substrate materials are polymers, examples of which are polyvinyl chloride, polyethylene, and polypropylene, in the form of a nonporous sheet. Biaxially oriented high-density polyethylene is presently preferred.

Application of the active ingredient formulation to the substrate is achieved by any conventional application method, such as dipping, brushing, spreading with a doctor blade, or spraying. The solvent is then allowed to evaporate, leaving a solid layer on at least one side, and preferably both sides, of the substrate.

The quantity of active ingredient contained on the coated substrate is not critical to the invention and can vary. In most cases, however, best results will be obtained with a weight percent range of about 0.01% to about 10.0% of the active ingredient relative to the substrate plus the coating of formulated active ingredient. A preferred range is from about 0.5% to about 3.0%. In the type of formulation above with a polyethylene sheet as the substrate, the nithiazine preferably constitutes from about 0.90% to about 1.1% by weight of the coated substrate, or from about 0.26 mg/cm$^2$ (of substrate surface) to about 0.32 mg/cm$^2$. Once the appropriate amount of slurry is applied, the solvent is removed by drying the coating in a conventional manner. For the formulation shown, a drying oven operating at a temperature of 120° C. provides satisfactory results.

The preferred attractant composition is a mixture of ingredients, at least two of which are a trialkylamine salt and a $C_2$–$C_{18}$ carboxylic acid or its alkali salt. Preferred trialkylamines are those in which the alkyl groups are ethyl or methyl, with trimethylamine particularly preferred. The salt is preferably a hydrohalide or a hydrosulfate salt, with hydrohalides particularly preferred. Trimethylamine hydrochloride is the most preferred. Suitable carboxylic acids include linear, branched, saturated and unsaturated carboxylic acids. Preferred carboxylic acids are propionic, butyric and isobutyric. Preferred alkali metals to form the salts of these acids are lithium, sodium and potassium. Sodium n-butyrate is a particularly preferred species.

Further preferred attractant compositions are those that contain a sex pheromone in addition to the trialkylamine salt and the carboxylic acid. Examples of sex pheromones are:

(Z)-7,8-epoxy-2-methyloctadecane (E)-8,(E)-10-dodecanetriol (Z)-9-tetradecenal (E)-11-tetradecenal (Z)-11-hexadecenal (Z,Z)-11,13-hexadecadienal (E)-5-decenyl acetate (Z)-7-dodecenyl acetate (E,Z)-10,12-hexadecadienal (Z)-8-dodecenyl acetate (Z)-9-dodecenyl acetate (E)-10-dodecenyl acetate (Z)-9-tetradecenyl acetate (Z)-11-tetradecenyl acetate (E)-11-tetradecenyl acetate (Z)-9,(E)-11-tetradecadienyl acetate (Z)-9,(E)-12-tetradecadienyl acetate (Z)-7,(Z)-11-hexadecadienyl acetate (Z)-3,(Z)-13-octadecadienyl acetate
(E)-3,(Z)-13-octadecadienyl acetate
(Z)-9-tricosene (Z)-9-Tricosene, commonly known as Muscalure, is preferred, particularly for house flies.

The relative amounts of the attractants, whether only two or all three are included, can vary while still achieving the attractant effect. In preferred embodiments of the invention, however, each of the three components comprises at least about 10% by weight of the attractant composition, more preferably from about 10% to about 50% by weight, and most preferably from about 10% to about 35% by weight. When the attractant composition consists of (Z)-9-tricosene, n-butyric acid and trimethylamine, the preferred weight percent ranges are 18%–58% for the (Z)-9-tricosene, 29%–70% for the n-butyric acid, and 12.5%–53% for the trimethylamine. One presently preferred composition contains approximately 20% (Z)-9-tricosene, 33% n-butyric acid, and 14% trimethylamine (all by weight).

The breakable shell containing the attractant composition can be of any material or construction. One example is a vial of soda-lime glass, sealed after being filled with the attractant composition, and enclosed in a protective sleeve. The sleeve protects the vial against premature breakage and, once the vial is broken, serves as a wicking device to enhance the volatilization of the attractant components. An example of such a sleeve is one constructed of a fibrous polymer covered with paper; another example is an absorbent polymer or paper sleeve enclosed by a knitted sock mesh.

A plan view of an example of a device in accordance with this invention appears in FIG. 1, which shows the components of the device, including the insecticide-coated sheet 11, two capsules of attractant composition 12, 13, and the housing 14. The sheet 11 is a thin, rectangular sheet of nonporous plastic, coated on both sides with the solid nithiazine formulation, and the capsules 12, 13 are sealed cylindrical glass ampoules each containing the entire combination of components included in the attractant composition. The housing 14 has a rectangular area 15 that is raised on one side to form a shallow internal rectangular compartment of dimensions slightly larger than those of the insecticide-coated sheet 11. The housing also has two smaller elongated areas 16, 17, one at each end (i.e., the opposing shorter edges) of the rectangular compartment, the two smaller areas also raised to one side of the housing but forming rounded compartments roughly conforming to the contours of, but slightly larger than, the ampoules 12, 13. The raised areas are sufficiently flexible that they can be manually compressed to break the ampoules inside and release the attractant vapors.

Figure 2:
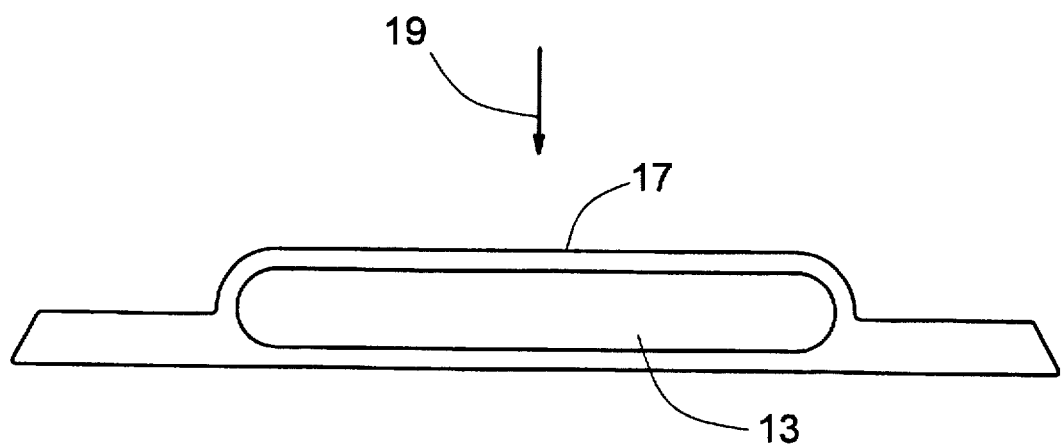
FIG. 2 is a cross section of a portion of the device of FIG. 1, taken along the line 2—2 of FIG. 1.

FIG. 2 is a cross section of one of the ampoules 13 and the compartment 18 in which it is retained. Breakage of the ampoule to release the attractant vapors is achieved by finger pressure on the raised portion 17 of the housing in the direction of the arrow 19.

Returning to FIG. 1, the insecticide sheet compartment is perforated by an array of openings 21 that expose the underlying sheet to insects approaching the housing from outside, and identical openings in the same array are located on the opposite face of the housing (not visible in the view shown in FIG. 1). Along one straight edge of each of the two ampoule compartments are rows of smaller openings 22 communicating with the compartment interiors, and thereby providing vent holes for the attractant vapors when the ampoules are crushed. Again, openings identical to these are located on the opposite face of the housing.

Additional features of the housing are rows of mounting holes 23 at each end of the housing to facilitate mounting of the device to a wall or suspending the device from a structure. Also, two areas facing each other approximately at the center of the two longitudinal edges of the housing are left non-perforated 24, 25, to permit handling of the device without the user's hands being placed in contact with the insecticide-coated surface.

The sizes and arrangement of the openings 21 that provide access to the insecticide-coated sheet are not critical and can vary widely, provided that they provide efficient utilization of the surface area of the sheet and the insecticide in the coating. It is also preferred that the openings be arranged to prevent flies from traveling along the housing surface without crossing the openings. Thus, the widths of the regions between adjacent openings when following a straight-line path of travel along the housing surface are preferably less than the width of a typical fly. In one presently preferred embodiment, the holes are approximately 0.25 inch (6.4 mm) in diameter, spaced approximately 0.08 inch (2.0 mm) apart. Likewise, the dimensions of the housing can vary widely. In the presently preferred embodiment, the housing is approximately 18 inches (46 cm) in length and 4.62 inches (11.7 cm) in width, with the insecticide sheet compartment being approximately 14.5 inches (36.8 cm) in length and 4 inches (10.2 cm) in width. The ampoule dimensions are approximately 42 to 50 mm in length and 6.5 to 8.0 mm in diameter. The portions of the housing other than the ampoule-retaining regions are preferably less than about 1.0 cm in thickness.

To enhance the appeal of the device to insects, the housing and the coating on the sheet are preferably in bright, contrasting colors. One example is a yellow coating against a red housing.

Figure 3:
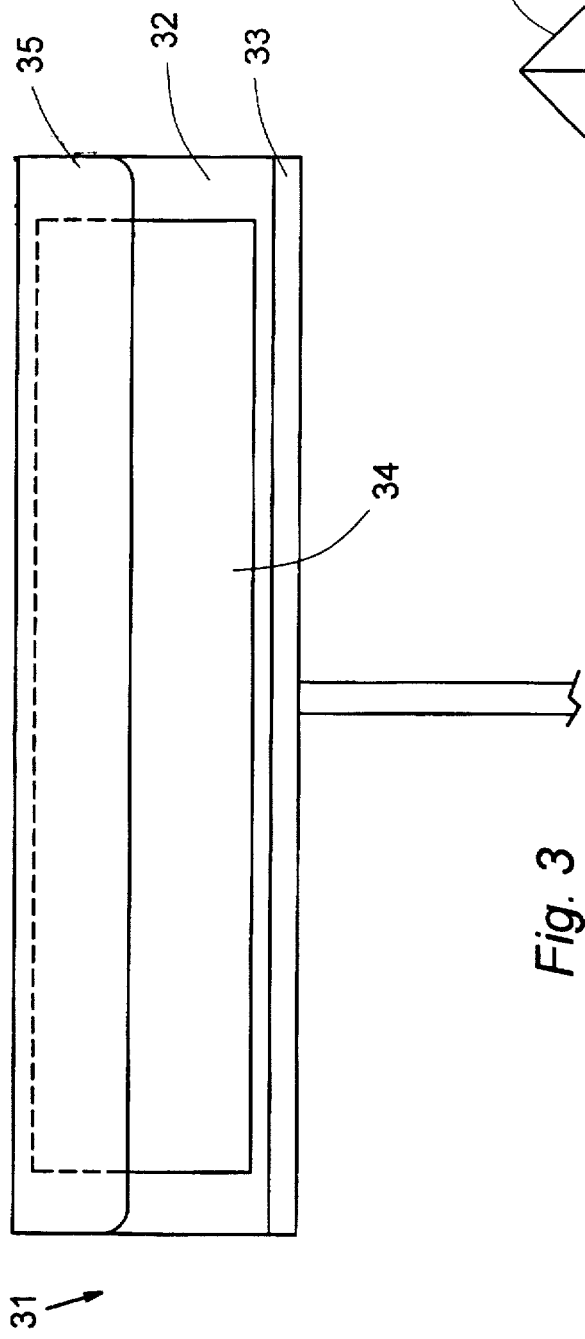
FIG. 3 is a mounting station for the device of FIG. 1.
Figure 4:
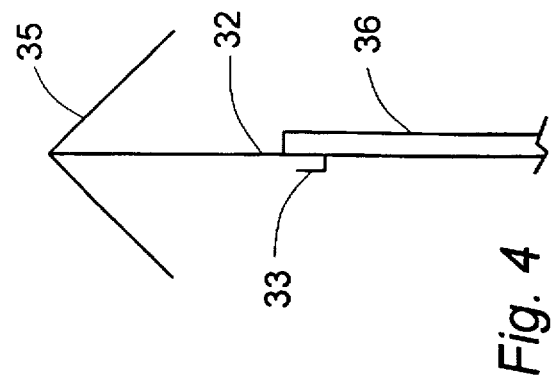
FIG. 4 is an end view of the mounting station of FIG. 3.

While the device as a whole can be mounted to or suspended from structures of a variety of shapes and contours, FIGS. 3 and 4 show one example of a mounting structure or support 31 designed for placement in an open field. The support consists of a mounting frame 32 of approximately the same dimensions as the housing (not shown), with a trough 33 along the lower edge of the frame on one side, and a rectangular opening or window 34. The device is placed on one side of the frame by inserting the lower edge of the housing in the trough 33. This leaves one full side of the housing exposed to the atmosphere, while the other side is exposed through the window 34, thereby permitting access to all active surfaces of the device. A roof 35 slanted downward on both sides of the frame serves a multitude of functions: protecting the active ingredient in the insecticide coating from sunlight, since ultraviolet light promotes decomposition of the active ingredient; shielding the coating from rain and water sprays since certain components of the coating may be water-soluble; protecting the coating from livestock (and protecting livestock from the coating); and making the coating more attractive to flies by providing shade for the flies to alight on. A stake 36 or other support permits the mounting structure to be secured in the ground.

The housing, with insecticide-coated sheet and ampoules contained inside, is preferably sealed in a protective sheath or covered with a protective covering when not in use. Useful coverings that will preserve the activity of the active ingredients and prolong the shelf life are those that are impermeable to moisture and that shield the device against oxygen and ultraviolet light. Foil laminates or other suitable materials that will be readily apparent to those skilled in the art will serve these purposes effectively. A desiccant is also preferably included in the packaged device as a further means of preventing or retarding decomposition of the active ingredients.

The foregoing is offered primarily for purposes of illustration. It will be readily apparent to those skilled in the art that the materials, dimensions, configurations, and other parameters of the device described herein may be further modified or substituted in various ways without departing from the spirit and scope of the invention.

We claim:

1. A device for attracting and killing insects, comprising:

a solid sheet of nonabsorptive material coated with a solid layer comprising a tetrahydro-2-(nitromethylene)-2H-1,3-thiazine insecticide; and an attractant composition encapsulated in a breakable shell;

said coated solid sheet and said breakable shell retained in a flat, substantially planar housing with openings exposing regions of said solid sheet, a compressible cavity to receive said breakable shell, and ports adjacent to said cavity to permit the escape of vapors therefrom to the atmosphere.

2. A device in accordance with claim 1 in which said attractant composition is a mixture comprising a trialkylamine salt and a $C_2$–$C_{18}$ carboxylic acid or an alkali salt thereof.

3. A device in accordance with claim 1 in which said attractant composition is a mixture comprising a trialkylamine salt, a $C_2$–$C_{18}$ carboxylic acid or an alkali salt thereof, and a pheromone.

4. A device in accordance with claim 1 in which said attractant composition is a mixture comprising a trimethylamine hydrochloride, n-butyric acid, and muscalure.

5. A device in accordance with claim 1 comprising a plurality of said attractant compositions each encapsulated in an individual breakable shell and retained in a separate compressible cavity in said housing.

6. A device in accordance with claim 1 in which said tetrahydro-2-(nitromethylene)-2H-1,3-thiazine insecticide is the compound tetahydro-2-(nitromethylene)-2H-1,3-thiazine.

7. A device in accordance with claim 1 in which said solid sheet of nonabsorptive material is a nonporous polymer.

8. A device in accordance with claim 7 in which said nonporous polymer is a member selected from the group consisting of polyvinyl chloride, polyethylene, and polypropylene.

9. A device in accordance with claim 1 in which said housing and said solid layer containing a tetrahydro-2-(nitromethylene)-2H-1,3-thiazine insecticide are of contrasting colors to enhance the attraction of insects to said device.

10. A device in accordance with claim 1 in which said solid layer further comprises a dye rendering said layer lighter in color than said housing.

11. A device in accordance with claim 1 in which said housing other than said compressible cavity is less than 1.0 cm in thickness.

12. A device in accordance with claim 1 further comprising a mounting frame for said device, means for retaining said device in said mounting frame, and means for sheltering said device thus retained from sunlight and rain.

* * * * *